(12) United States Patent
Juan et al.

(10) Patent No.: US 10,736,684 B1
(45) Date of Patent: Aug. 11, 2020

(54) MINIATURE INDUCTIVE HEATING DEVICE

(71) Applicants: Eduardo J. Juan, Cabo Rojo, PR (US); Madeline Torres-Lugo, Cabo Rojo, PR (US); Jorge L. Castro-Torres, Las Piedras, PR (US)

(72) Inventors: Eduardo J. Juan, Cabo Rojo, PR (US); Madeline Torres-Lugo, Cabo Rojo, PR (US); Jorge L. Castro-Torres, Las Piedras, PR (US)

(73) Assignee: University of Puerto Rico, San Juan, PR (US)

( * ) Notice: Subject to any disclaimer, the term of this patent is extended or adjusted under 35 U.S.C. 154(b) by 374 days.

(21) Appl. No.: 15/903,171

(22) Filed: Feb. 23, 2018

Related U.S. Application Data

(60) Provisional application No. 62/462,623, filed on Feb. 23, 2017.

(51) Int. Cl.
*A61B 18/08* (2006.01)
*H05B 6/06* (2006.01)
*H05B 6/42* (2006.01)
*A61B 18/00* (2006.01)

(52) U.S. Cl.
CPC ............. *A61B 18/082* (2013.01); *H05B 6/06* (2013.01); *H05B 6/42* (2013.01); *A61B 2018/00023* (2013.01); *A61B 2018/00178* (2013.01); *A61B 2018/00815* (2013.01); *A61B 2018/00821* (2013.01); *A61B 2018/00875* (2013.01); *A61B 2018/00982* (2013.01)

(58) Field of Classification Search
CPC ........ A61B 18/082; A61B 2018/00023; A61B 2018/00982; A61B 2018/00178; A61B 2018/00875; A61B 2018/00815; A61B 2018/00821; H05B 6/42; H05B 6/362; H05B 6/06
See application file for complete search history.

(56) References Cited

U.S. PATENT DOCUMENTS

| 2,283,285 | A | * | 5/1942 | Pohlman | A61H 23/0245 601/2 |
|---|---|---|---|---|---|
| 6,074,385 | A | * | 6/2000 | Klopotek | A61B 18/14 128/898 |
| 2004/0122494 | A1 | * | 6/2004 | Eggers | A61F 7/12 607/103 |
| 2006/0122590 | A1 | * | 6/2006 | Bliweis | A61B 18/082 606/24 |
| 2007/0078453 | A1 | * | 4/2007 | Johnson | A61B 18/1482 606/32 |
| 2008/0161797 | A1 | * | 7/2008 | Wang | A61B 18/1492 606/41 |

(Continued)

*Primary Examiner* — Patrick M. Buechner
(74) *Attorney, Agent, or Firm* — Hoglund & Pamias, PSC; Roberto J. Rios

(57) ABSTRACT

An induction heating coil is positioned inside a tube-like instrument having dimensions similar to current laparoscopic instruments. Magnetic field intensities of up to 15 kA/m at a frequency of 289 kHz are achieved while the instrument is operated at safe temperatures. A cooling agent system maintains a desired temperature inside the instrument and temperatures sensors monitor the temperature of the cooling agent as well as the temperature of the induction heating coil to safely operate the instrument within operating temperatures.

20 Claims, 9 Drawing Sheets

(56) References Cited

U.S. PATENT DOCUMENTS

| | | | |
|---|---|---|---|
| 2008/0249350 A1* | 10/2008 | Marchitto | A61N 2/02 600/10 |
| 2008/0266203 A1* | 10/2008 | Rossetto | A61B 18/1815 343/895 |
| 2011/0077451 A1* | 3/2011 | Marchitto | A61N 2/02 600/13 |
| 2013/0085497 A1* | 4/2013 | Chang | A61B 17/32 606/45 |
| 2017/0135742 A1* | 5/2017 | Lee | A61B 18/082 |

* cited by examiner

Figure 6a
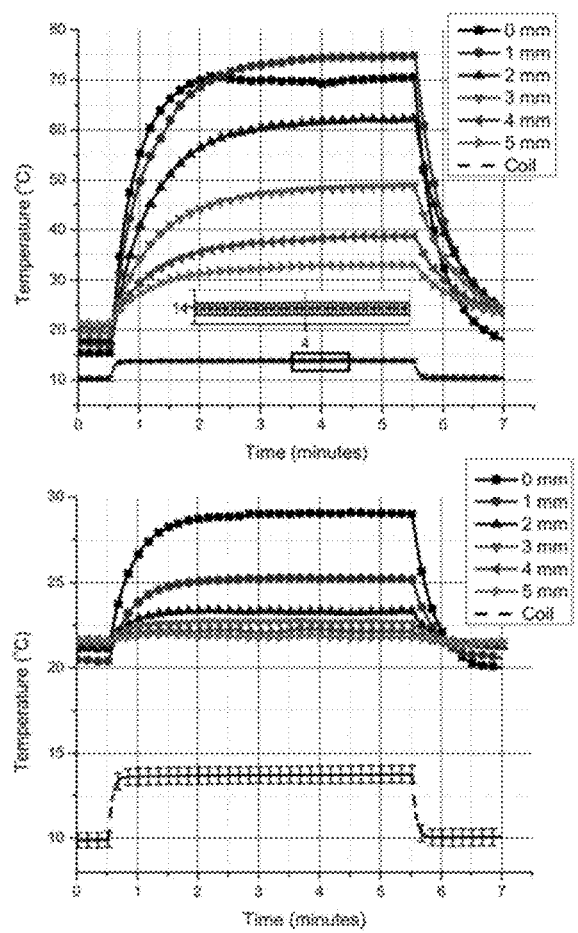
Figure 6b
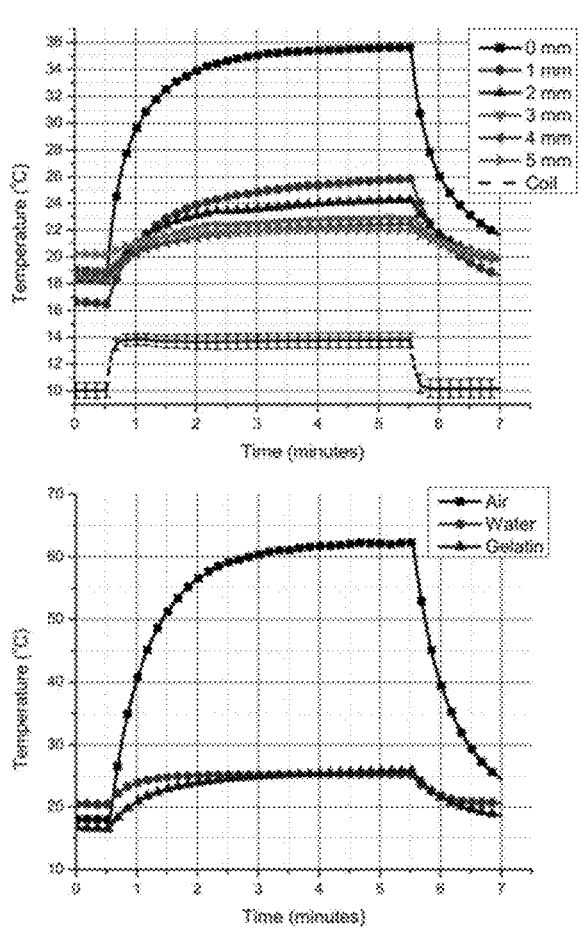
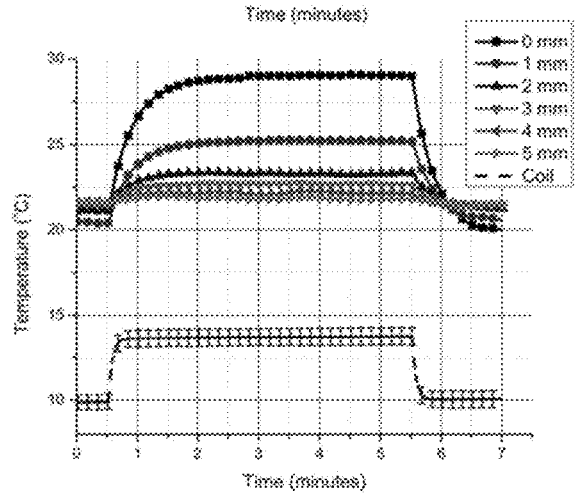
Figure 6c
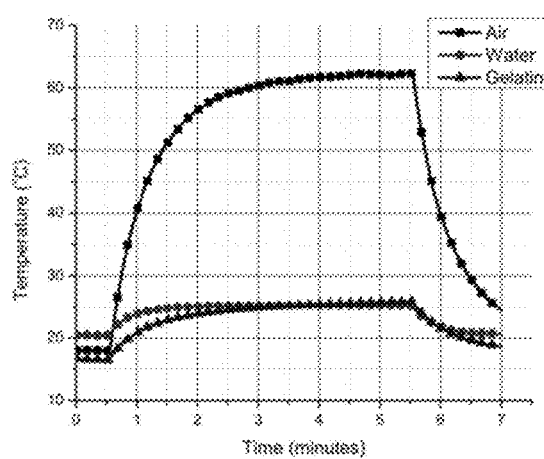
Figure 6d

Figure 6e
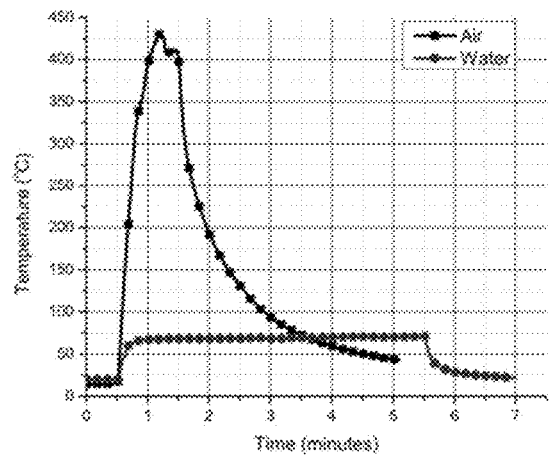
Figure 6f
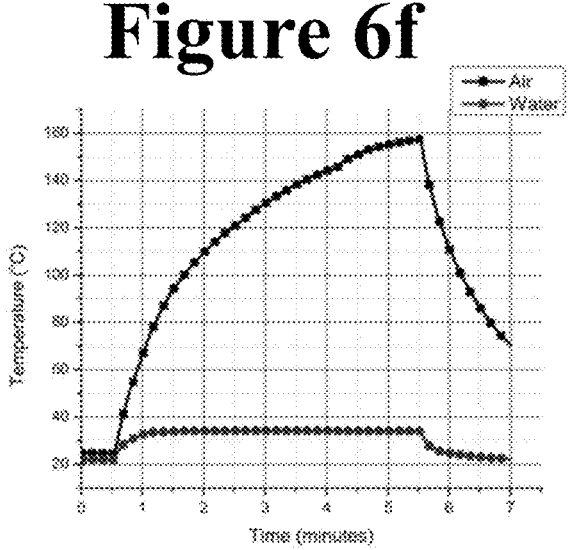
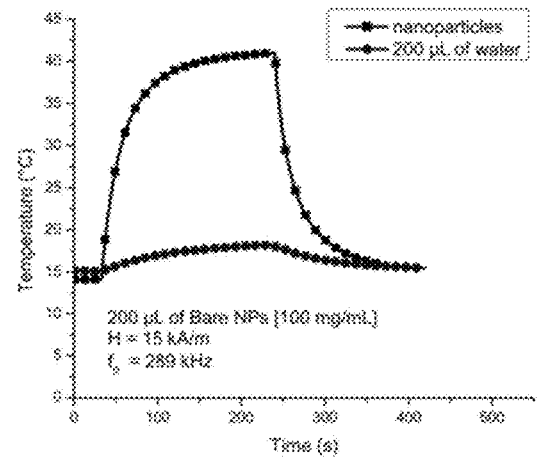
Figure 6g

MINIATURE INDUCTIVE HEATING DEVICE

GOVERNMENT INTEREST

The claimed invention was made with U.S. Government support under grant numbers: HRD-0833112 and HRD-1345156 awarded by The National Science Foundation (NSF) and grant number: U54 CA 96300/u54 ca 96297 awarded by The National Institutes of Health (NIH). The government has certain rights in this invention.

BACKGROUND OF THE INVENTION

Induction heating has been the scope of many researchers around the globe for domestic, industrial or medical applications. Its efficient, safe, clean, and accurate delivery of energy to a target (metal or other conductive material) has interested researchers in this type of technology. Specifically, the characteristics and the advantages of this technology has led researchers to investigate its potential use in cancer treatments and other clinical applications for treating patients suffering from this disease. Many of the proposed approaches include the use of induction heating designs with the goal of delivering heat to the tumor by subjecting magnetic nanoparticles to an alternating magnetic field. This type of treatment is known as Magnetic Fluid Hyperthermia (MFH) and refers to the temperature elevation (43-47° C.) of the affected area by means of a ferrofluid. Recently, Connord and colleagues (2015) built a miniature electromagnet (19 mm internal diameter, 29 mm external diameter, and a 400 μm airgap) to conduct MFH experiments on living cells under a confocal microscope and study the biological responses induced by the alternating magnetic field in combination with magnetic nanoparticles. Subramanian et al. (2016) also designed a miniature coil for the same purposes, only that this one was used inside an incubator. However, there are few miniature designs like these available nowadays. Moreover, many of these applications have several drawbacks that ultimately affect the implementation of such procedures. Therefore, the side effects associated with the treatments can be greatly decreased by reducing the instrument used in MFH applications down to a size that only affects the tumor.

SUMMARY OF THE INVENTION

The present invention provides a miniature induction heating instrument for heating electrically conductive materials (magnetic nanoparticles, medical devices, etc.) inside a body cavity or other hard to reach enclosure or spaces.

According to an aspect of the invention, a miniature inductive heating device is provided having an elongated body with a proximal end wall and a distal end wall opposite to the proximal end wall and a multilayer pancake coil positioned inside the elongated body and in contact with the distal end wall.

According to another aspect of the invention, the miniature inductive heating device includes a first thermal sensor positioned inside said multilayer pancake coil and a second thermal sensor positioned inside the elongated body.

According to still another aspect of the invention, a cooling agent inlet port and a cooling agent outlet port are positioned at the proximal end of the elongated body.

According to yet another aspect of the invention, an electric wiring port is positioned at the proximal end of the elongated body.

According to one aspect of the invention, electrical wires coming from the first thermal sensor, the second thermal sensor and the multilayer pancake coil exit the elongated body through the electric wiring port.

According to another aspect of the invention, a cooling agent is contained inside the elongated body and is in contact with the multilayer pancake coil.

In accordance to still another aspect of the invention, the cooling agent enters the elongated body through the cooling agent inlet port and exits the elongated body through the cooling agent outlet port.

According to yet another aspect of the invention, the cooling agent inlet port is positioned along or perpendicular to a longitudinal axis of the elongated body.

According to an aspect of the invention, the electric wiring port is positioned along or perpendicular to a longitudinal axis of the elongated body.

According to another aspect of the invention, the cooling agent outlet port is positioned perpendicular to a longitudinal axis of the elongated body.

According to another aspect of the invention, at least one of the elongated body and the distal end wall is made of a polymeric material.

According to still another aspect of the invention, the cooling agent inlet port includes a cooling agent tube positioned inside the elongated body so that an output of the cooling agent tube is in close proximity to the multilayer pancake coil.

According to yet another aspect of the invention, the first and second thermal sensors are thermistors and the second thermal sensor is positioned at the output of the cooling agent tube.

According to one aspect of the invention, the electrical cables from the multilayer pancake coil are connected to an impedance matching circuit and the electrical cables from the first and second thermal sensors are connected to a data acquisition system.

In accordance to another aspect of the invention, the cooling agent inlet port is connected to a cooling agent pump and the cooling agent outlet port is connected to a cooling agent reservoir.

According to still another aspect of the invention, the cooling agent is chilled water.

In accordance with yet another aspect of the invention, the cooling agent is maintained at a temperature between about −15° C.-20° C.

According to an aspect of the invention, a signal waveform generator device provides a signal to the impedance matching circuit.

According to another aspect of the invention, a processing unit receives from the data acquisition system temperature data associated to temperature measurements of the first and second thermal sensors and further controlling at least one of: the flow rate of the cooling agent, the temperature of the cooling agent and the power provided to the multilayer pancake coil.

According to still another aspect of the invention, the multilayer pancake coil has an outer diameter of about 8-11 mm and generates a magnetic field intensity of up to 30 kA/m at a frequency of 100-500 kHz.

According to yet another aspect of the invention, the temperature of the multilayer pancake coil is maintained at about 5° C.-20° C.

BRIEF DESCRIPTION OF THE DRAWINGS

Further features and advantages of the invention will become apparent from the following detailed description taken in conjunction with the accompanying figures showing illustrative embodiments of the invention, in which:

FIG. 6a-6g show plots of the induction heating of a stainless-steel disk in different media and uncoated SPIONs, according to the present invention.

Throughout the figures, the same reference numbers and characters, unless otherwise stated, are used to denote like elements, components, portions or features of the illustrated embodiments. The subject invention will be described in detail in conjunction with the accompanying figures, in view of the illustrative embodiments.

DETAILED DESCRIPTION OF THE INVENTION

Figure 1:
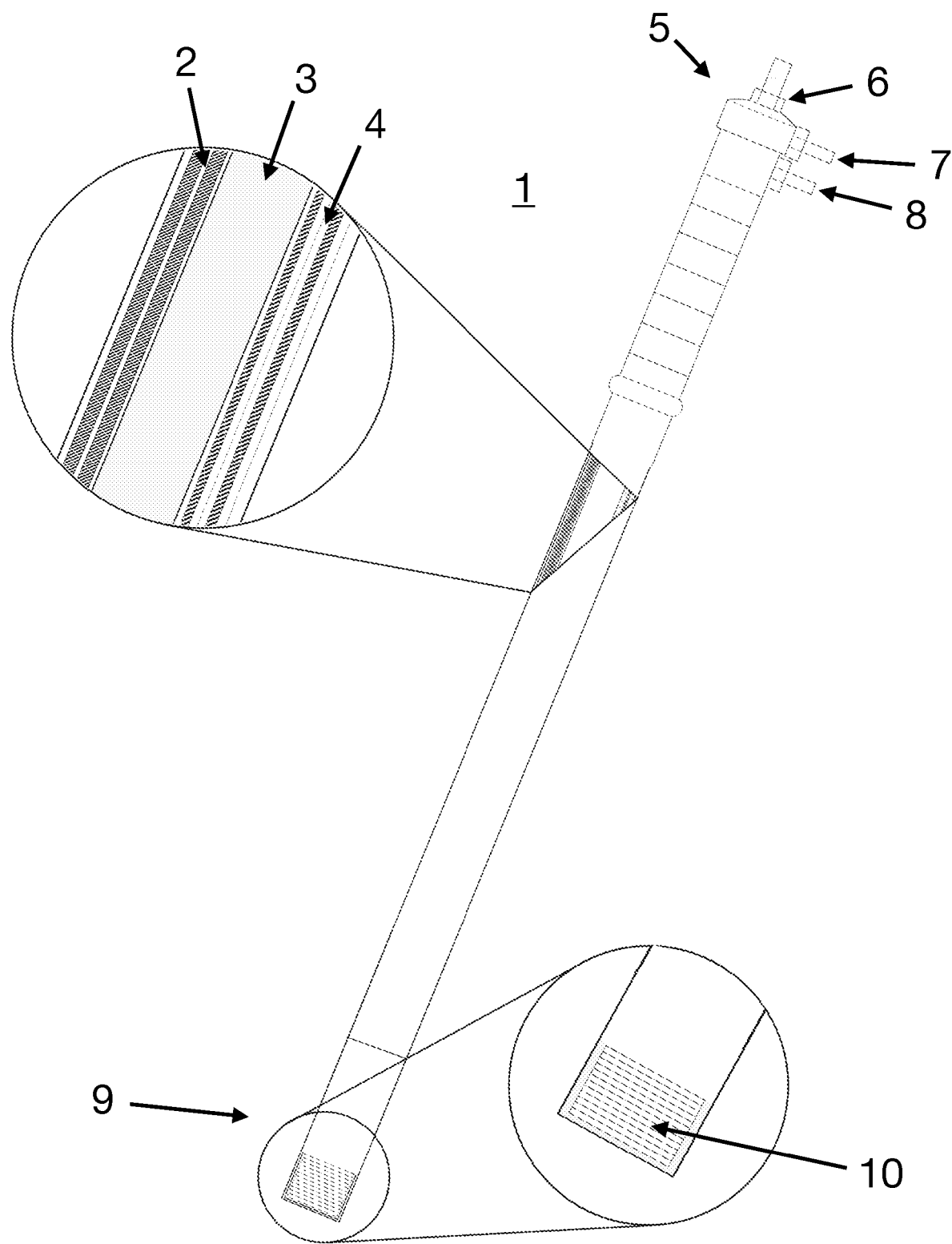
FIG. 1 shows a laparoscopic instrument according to the present invention.

The present invention provides a novel instrument that generates an alternating magnetic field for the generation of heat. Specifically, the instrument can be used in various industrial, domestic, and medical applications including the treatment of deep-seated tumors during laparoscopic surgeries. The instrument 1 is comprised of two main components: 1) a single miniature pancake coil to generate an alternating magnetic field, and 2) a long enclosure arrangement as show in FIG. 1. The instrument has an enclosure including thermocouples 2 to monitor the temperatures of the magnetic field generator and water circulating through it, a tube 3 connecting the inside of the enclosure to the external water source, and terminals 4 from the magnetic field generator comprising a coil 10. On the exterior of the enclosure, fittings 6, 7, and 8 are provided correspond to the electrical input/output connector, water inlet, and water outlet respectively. These fitting are provided to allow connecting the instrument of the present invention to any necessary external components.

According to the present invention, instrument 1 is connected to an external control unit 23 that includes an impedance matching circuit 20 that is selectively controlled to operate at a specified frequency, and to a data acquisition system 21 that monitors the temperatures measured by the thermocouples 6b, 6c inside the instrument 1. A cooling agent is circulated through the enclosure to remove the heat dissipated by the coil, effectively controlling the internal temperature of the instrument 1 while protecting its components from damage. In a preferred embodiment of the invention, chilled water is used as the cooling agent.

Figure 2:
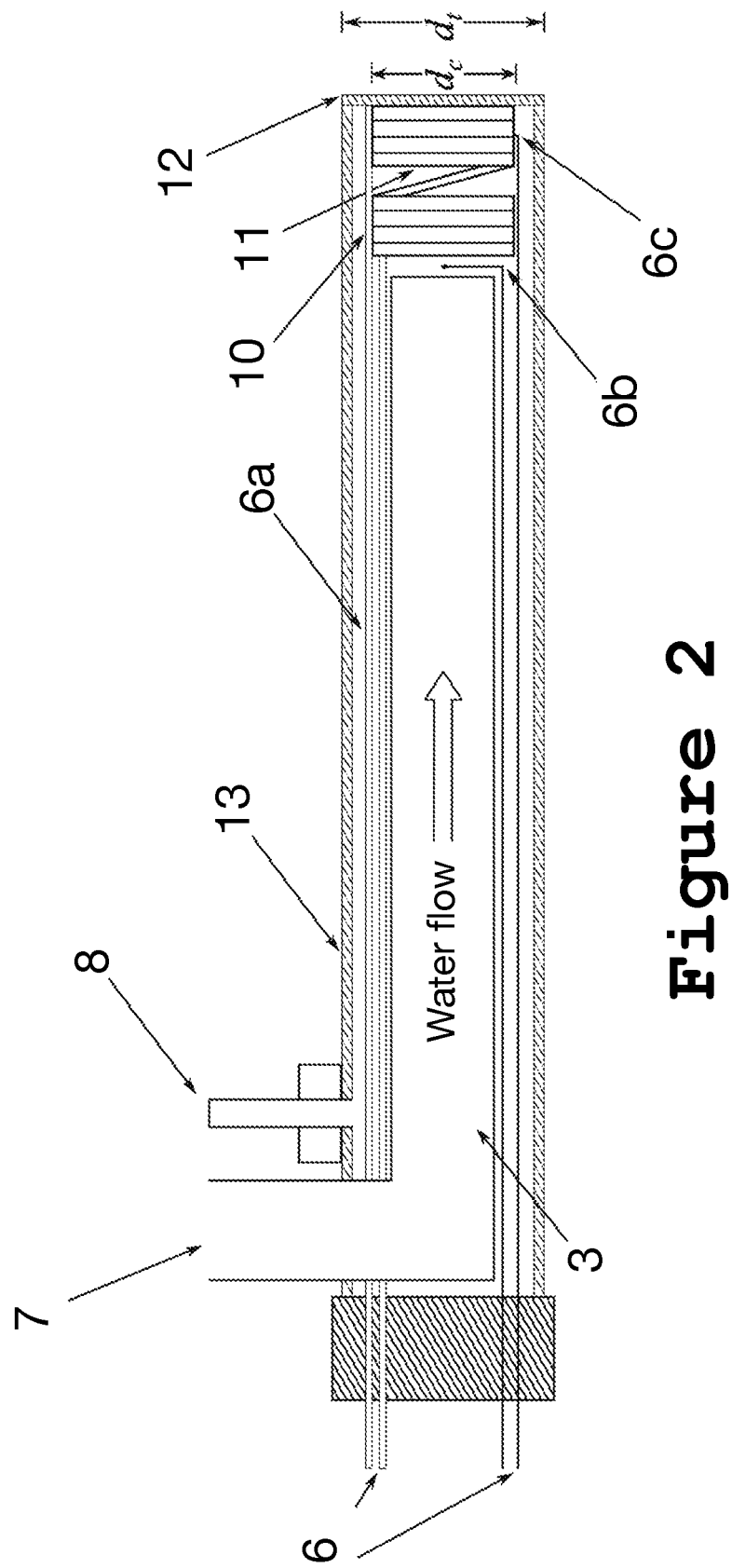
FIG. 2 shows a preferred embodiment of the laparoscopic instrument according to the present invention.
Figure 3:
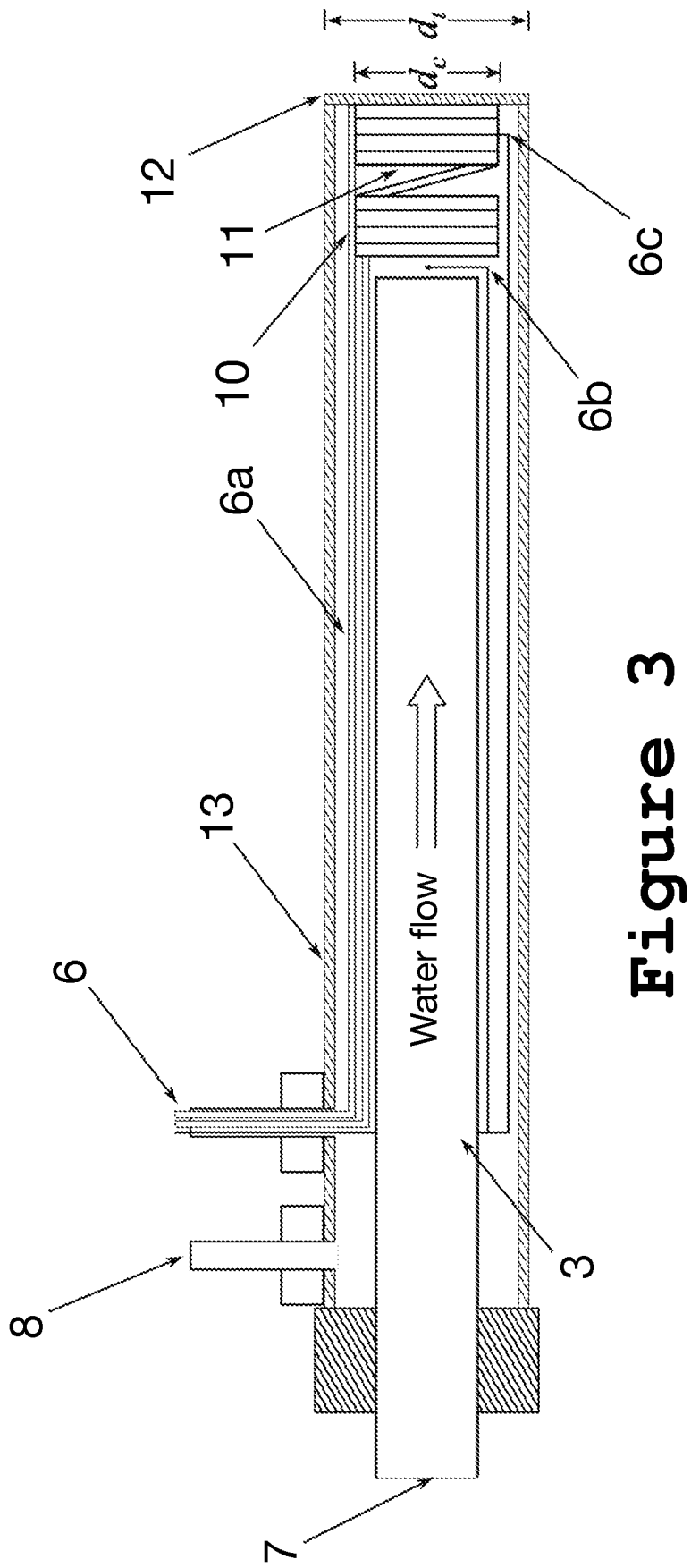
FIG. 3 shows another preferred embodiment of the laparoscopic instrument according to the present invention.
Figure 4:
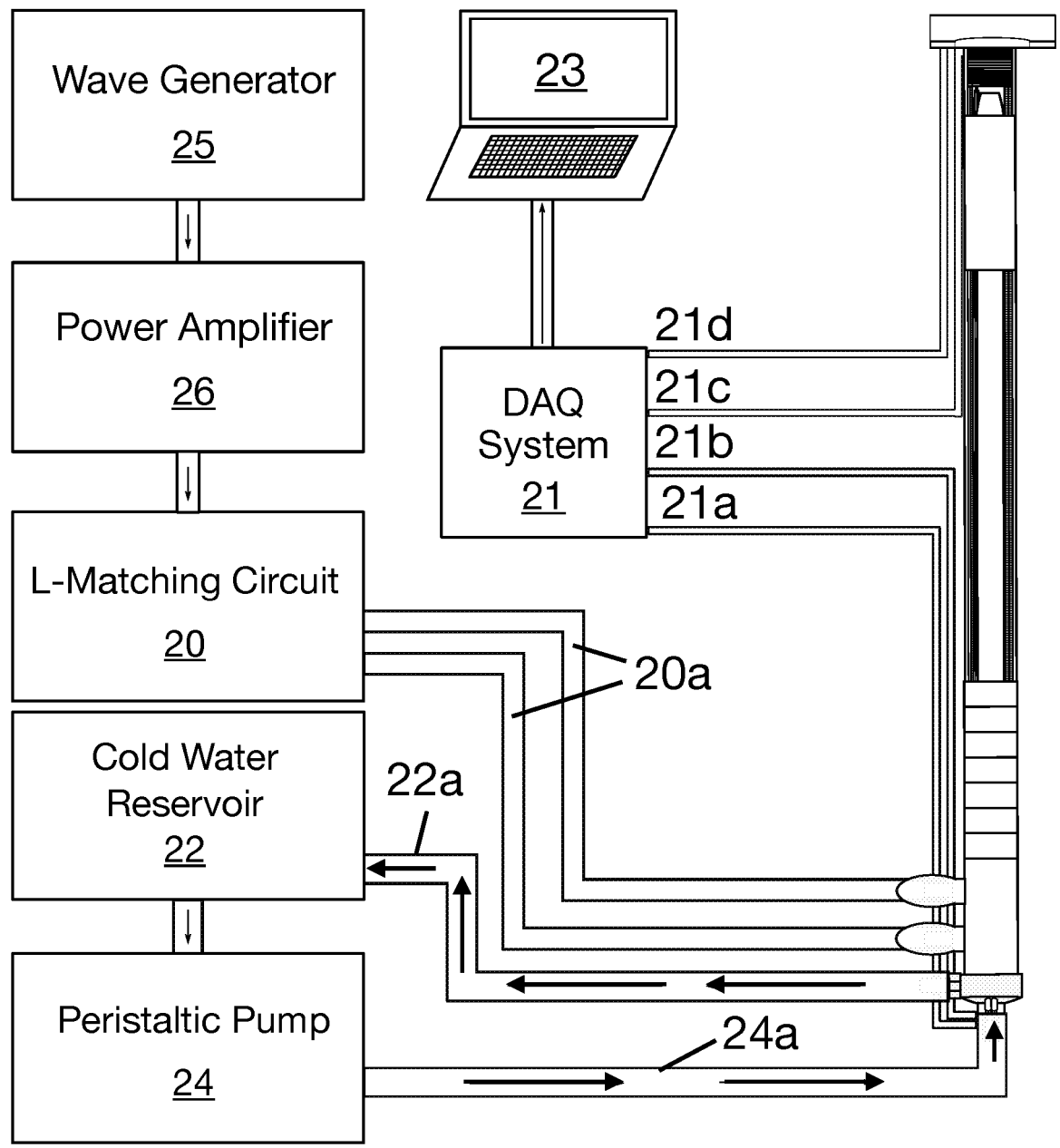
FIG. 4 shows a laparoscopic instrument system according to the present invention.

FIGS. 2-4 illustrate the instrument 1 according to the present invention. A single long enclosure is provided to house all the components of the instrument 1 which includes at its proximal end 5 a fitting 6 configured to be connected to a control unit 23 that includes an impedance match circuit 21 and a data acquisition system 21. The control unit 23, the impedance match circuit 21 and a data acquisition system 21 can be integrated into a single unit or provided as separate units electrically connected.

A water reservoir 22 is connected to the water inlet fitting 7 and water outlet fitting 8 as shown in FIG. 4. Instrument 1 is controlled through the use of thermocouples 6b, 6c, the impedance match circuit 20 and the data acquisition system 21 in order for the coil to be able to generate an alternating magnetic field which produces heat. The thermocouples 6b, 6c provide a temperature measurement which is electrically transmitted to data acquisition system 21 which monitors the internal temperatures of the water and the coil 10. Accordingly, the system selectively controls the power provided to the coil 10 in order to maintain a desired internal temperature. Alternatively, the control unit 23 also controls the temperature and circulating flow rate of the chilled water to maintain the desired internal temperature based on the measurements from the water and coil thermistors with the aid of a controlling interface 24.

As can be appreciated from the Figures, the coil has a diameter (dc) and is positioned at the distal end 9 of the enclosure of instrument 1. According to a preferred embodiment of the invention, the distal end 9 is sealed with a transparent circular sheet 12 having a diameter (dt) equal to the enclosure's diameter. The sheet 12 must be as thin as possible to allow the magnetic field to effectively affect the target of interest. A thick sheet 12 would make the instrument 1 to operate poorly, as the magnetic field will not necessarily reach the desired area, or it will not cover the area completely. The coil terminals 6a, water thermocouple 6b and coil thermocouple 6c used for monitoring the temperatures of the water and coil, respectively, are configured to be removed from the instrument through the electrical input/output connector 6. According to an embodiment of the invention, chilled water will start to fill the tube 3 through the water inlet 7 and once the water fills the tube 3, it will start to return to the water reservoir 22 through the water outlet 8 by gravity.

FIG. 3 illustrates an instrument 1 similar to the one illustrated in FIG. 2 with the exception that the water inlet 7 and the electrical input/output 6 are provided at different positions. A rigid tube 3 is used instead of a flexible silicone tubing, which can be adapted to a silicone tubing for a chilled water source. The use of the rigid tube is an advantage of this embodiment as it makes the instrument more robust and eliminates the possibility of bending the silicone tubing of FIG. 2 during use.

The enclosure of the instrument 1 has dimensions similar to a laparoscope, since it needs to be fitted through a trocar cannula. Even though the instruments used for laparoscopic surgeries are usually made of stainless steel, this cannot be the case for instrument of the present invention as any metal surrounding the coil can be heated by the magnetic field generated by the coil. Therefore, medical grade plastics walls 13 are used for this application. Additionally, the plastic must be sterilized since it will be used in clinical applications.

The magnetic field generator of the present invention is wound with Litz wire, a special type of stranded wire that minimizes the skin and proximity effects normally encountered in conductors. The small diameter of this wire allows the construction of a miniature coil that can fit through a tube 3 with a diameter less than 15 mm. This type of wire has the advantage that it will not significantly increase its resistance in AC applications. An air gap 11 is provided between a first section and a second portion of the coil 10 as shown in FIGS. 2 and 3. However, due to the high currents that will be flowing through the coil, chilled water is used to maintain its operating temperature below a specified temperature defined by the manufacturer. The present invention provides a novel laparoscopic instrument that even with the use of a very small coil, it will generate a magnetic field strong enough to actuate on the area of interest, but at the same time small enough to avoid damage to surrounding healthy tissues. This minimally invasive technology can be used during laparoscopy surgeries, where the treatment of deep-seated tumors becomes difficult and regression of cancer is highly probable if the tumor is not removed completely.

A preferred embodiment of the invention will be explained in conjunction with FIGS. 4-7. The present invention is embodied as a laparoscopic instrument capable of generating a maximum high-frequency magnetic field of 15 kA/m, which has the potential for treatment of deep-seated tumors or other applications where such high-frequency magnetic field is beneficial. The performance of such instrument was evaluated by conducting experiments on a stainless-steel disk (12 mm diameter) and uncoated nanoparticles at a total particle weight concentration of 100 mg/mL. The several components of the system are discussed below.

Magnetic Field Generator Design

A 21-turn miniature multilayer "pancake" coil was wound around a nail (1.5 mm diameter), using Litz wire which is a conductor comprised of many twisted insulated strands that greatly minimizes the skin and proximity effects normally present in conductors at high frequencies by reducing the cross-sectional area of individual conductors. It also counters the increase of the conductor impedance at higher frequencies, as the wire will maintain an AC resistance similar to its DC resistance. The wire used has 120 strands of 42 AWG wire and it can be operated at frequencies ranging from 200 to 350 kHz. and can withstand temperatures up to 155° C. due to its polyurethane insulation. Nylon was used on the exterior to hold the strands. Leaving 40 cm of wire, to later solder electrical terminals, 21 turns were made around the nail, which was inserted on a 10 mm×10 mm thin sheet of wood. It must be noted that while we used in our experiment a nail and a sheet of wood as part of the preparation method, no supporting means could be used or alternatively, other types of supporting means could be used for winding the coil as long as a uniform coil arrangement is achieved. In addition, it is important to point out that other combinations of cable strands, sizes, frequencies and dimensions could be used depending on the specific application and rated capacity of the components used.

Normally, the diameter of the instruments used in a laparoscopic surgery ranges from about 5 to 12 mm, although larger diameter constructs can be commercially found. Therefore, for this particular application a millimeter grid paper was attached to the wood to ensure that the coil would have approximately 10 mm in diameter, although smaller diameters could be used preferably a diameter of about 8 mm could also be used. Note that small deviations from these diameters due to factors such as but not limited to the cable ratings are also encompassed by this diameter values.

After 10 turns, a precision fine wire "T" thermocouple was inserted close to the core of the coil to measure its core temperature during operation. Every three turns, adhesive material (Gorilla® Super Glue from Gorilla Glue Company®) was poured on the windings to maintain the turns in place. Afterwards, this coil was taken out of the base. Another 40 cm were left and the wire was cut from the spool. The Litz wire was soldered to 8 AWG electrical wire, and the connection was subsequently insulated with liquid electrical tape. Finally, ring terminals were crimped to the ends of the 8 AWG electrical wires. Table 1 below shows a list of all the measured parameters of the coil used for the laparoscopic instrument.

TABLE 1

| Parameters | Specification | Units |
| --- | --- | --- |
| Height (I) | 6.12 | mm |
| Outer diameter ($d_o$) | 11.05 | mm |
| Inner diameter ($d_i$) | 1.57 | mm |
| Turns (N) | 21 | unitless |
| Resistance ($R_C$) | 0.13 | Ohms |
| Inductance ($L_C$) | 3.01 | µH |

The use of a pancake coil is critical to the proper operation of the invention because some of the generated magnetic field appears on its surface and thus, it can be used in induction heating applications to heat other surfaces. In contrast, when other geometries like a helical configuration are used, the sample must be inserted inside the coil to be subjected to the magnetic field operating in a completely different manner than the instant invention.

Impedance Matching Network

Figure 7:
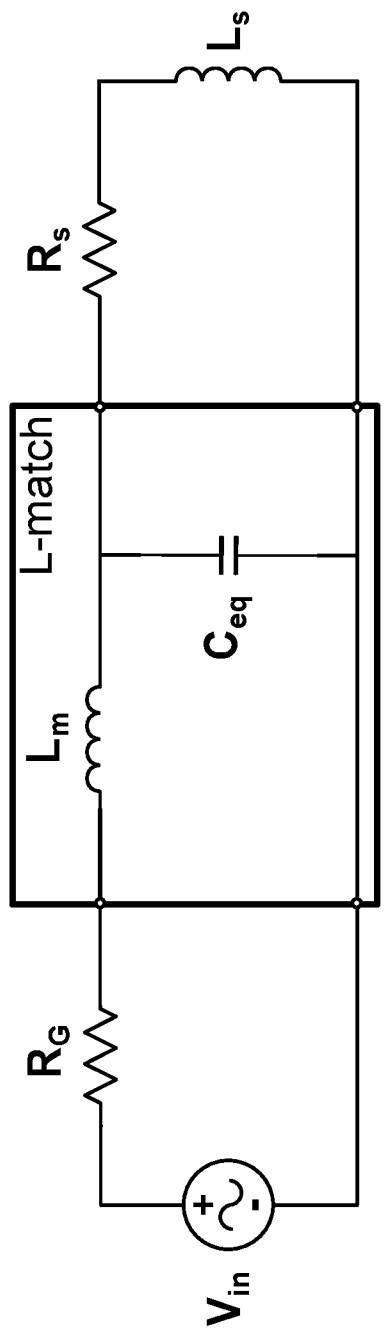
FIG. 7 illustrates a L-match configuration circuit, according to the present invention.

An L-match configuration circuit was used to operate the coil at the desired frequency. The important role of an impedance matching network is to convert a load impedance to be equal to the complex conjugate of the source impedance. By doing so, they will have equal real parts and opposite reactance, making the net reactance zero. Performing impedance matching results in maximum power transfer from the source to the load. For this particular application, the network was designed to operate at a resonance frequency (f) of 300 kHz. The final circuit model of the laparoscopic instrument, which shows a reversed L-section configuration, is shown in FIG. 7 where $R_G$ refers to the internal resistance of the generator, and $R_S$ and Ls are the resistance and inductance of the coil respectively. Table 2 below shows a list of the calculated values for the impedance matching network necessary to achieve a resonance frequency of 300 kHz with the laparoscopic instrument according to the present invention. It is to be noted that the components of the impedance matching circuit as well as their values could be selected to allow operating frequencies between 100 kHz-500 kH that are suitable for inductive heating applications.

TABLE 2

| Parameters | Specification | Units |
| --- | --- | --- |
| Matching inductance ($L_m$) | 52.01 | µH |
| Equivalent capacitance ($C_{eq}$) | 97.74 | nF |

The electrical components used for the matching inductance (Lm) and equivalent capacitance (Ceq) had values of 0.12 mH and 100 nF, respectively. Due to the high voltage drops and currents throughout the circuit, CSM 150 capacitors from Celem Power Capacitors Ltd. (Jerusalem, Israel) were used. These capacitors are rated at 150 kVA and can be used at high frequencies. The matching inductance was implemented using 10 AWG electrical wire. A resonance frequency of 279 kHz was achieved using these values.

Cooling System Design

A cooling system was used to maintain the internal temperature of the coil below 155° C. (maximum temperature the wire insulation can withstand) because of heat dissipation due to resistive losses from the coil. This system regulates the coil temperature by circulating cold water (5° C.-8° C.) throughout the instrument. In addition, all the cables and tubing were connected to the proximal end of the instrument, so that the instrument can be freely inserted through a trocar cannula into an abdomen of a patient.

A laparoscopic instrument, according to a preferred embodiment of the invention was constructed. In a preferred embodiment a polycarbonate tubing (½ in. tube inner diameter×⅝ in. outer diameter×1/16 in. wall) was provided to enclose the coil. However, other polymeric materials can be used that provides the same advantages. The length of the tube was approximately 34 cm. A distal end of the tube was sealed by cutting and using a piece of polycarbonate sheet (same diameter as the tube). The coil was fixed on the sheet before sealing with adhesive material such as marine epoxy. The terminals were then brought all the way to the proximal end of the tube and taken out through two male adapters (¼ in. outer diameter×⅛ in. MIP). The terminals were then soldered to 8 AWG wires and inserted into the adapters for holding the wires in place. Vacuum caps were provided to seal the adapters and were further reinforced with silicone and marine epoxy.

In order to circulate the water throughout the tube, a barbed fitting was introduced in a vacuum cap and 25 L/S tubing was inserted on the inside and outside of the cap. The inside tubing was cut so that it reached the coil ensuring that the water flows right through the coil before returning to the reservoir. Accordingly, an end of the inside tubing must be positioned in proximity to the coil as close as possible so as to ensure that the chilled water contacts the coil before exiting the tube. Thermocouples from the inside of the tube were inserted through a double lumen plastic tubing to reduce the possibility of water leaks, as the diameter of the holes was slightly larger than the diameter of the thermocouple. All possible leaking locations were sealed with silicone.

Experimental Setup

A 20 MHz 33220A function/arbitrary waveform generator 25 from Agilent Technologies® was connected and operated at the resonance frequency to generate the desired alternating magnetic field for the heating induction experiments. Amplification of the input signal was performed using an RF power amplifier 26 (E&I® 1000 W, model 1140LA) and the amplified signal was directly provided into the L-matching circuit 20 which was connected to the instrument 1 as shown in FIG. 4. Alternatively, the generated signal provided to the L-matching circuit 20 can be directly provided by a single signal waveform generator device already generating the signal with the desired power level. A peristaltic pump 24 was used to circulate cold water (5° C.-8° C.) from a reservoir 22 into the instrument 1 via water pipe 24a and excess water returned to the reservoir 22 via water pipe 22a once the instrument 1 was filled, thus removing heat dissipated by the coil due to resistive losses. However, the system can circulate water or any other cooling agent with a temperature between about −15° C.-20° C. depending on the specific application, the type of cooling agent used and its intrinsic properties, wherein it should be noted that small deviations from these limits due to factors such as but not limited to tolerances of the equipments are also encompassed by said range. A data acquisition (DAQ) system 21 (model NI 9211, in combination with a virtual instrument (VI) built in LabVIEW 14.0 software) was provided to record the temperatures from: the center of the coil, water inside the instrument, polycarbonate sheet where the coil was attached, and any experimental samples. All the thermocouples were connected to the analog inputs (21a-21d) of the DAQ system 21 and placed at the desired locations to read the temperatures, wherein analog input 21a was connected to the thermocouple located in the center of the coil, analog input 21b was connected to the thermocouple located to measure the water temperature inside the device, analog input 21c was connected to the thermocouple located at the polycarbonate sheet where the coil is attached and analog input 21d was connected to the thermocouple located at the sample. The output of the DAQ system 21 was then connected to a computer 23 through USB interface, where a custom-made VI was developed to acquire the temperature data associated to all the thermocouple measurements.

Results

Magnetic Field Profile

Several magnetic field measurements were made with a custom-made magnetic field sensor (air coil sensor) to obtain the magnetic field profile of the coil used. Characterizing the magnetic field generated by the instrument was of upmost importance, as it helped in the prediction of magnetic field intensities as a function of the axial and radial distance, and the current through the coil.

Figure 5A:
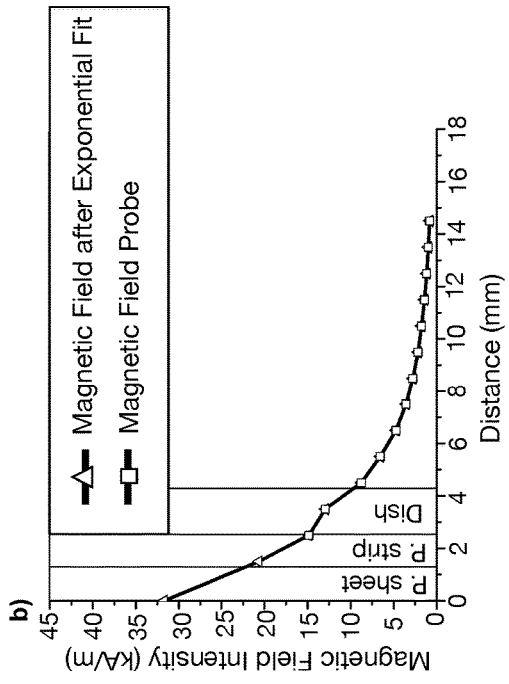
FIG. 5a-5c show plots for the magnetic field characterization of the laparoscopic instrument, according to the present invention.
Figure 5B:
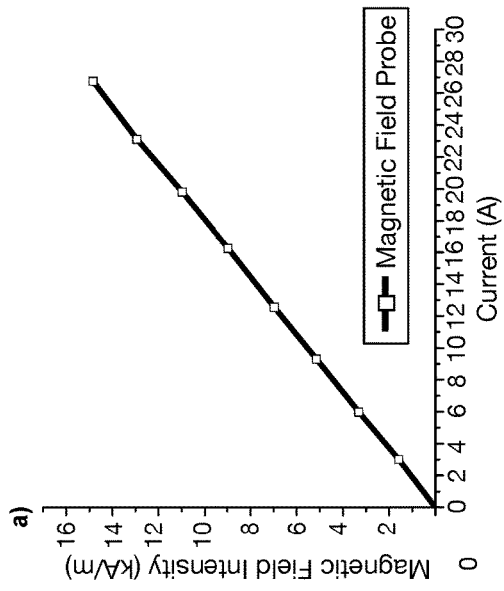
Figure 5C:
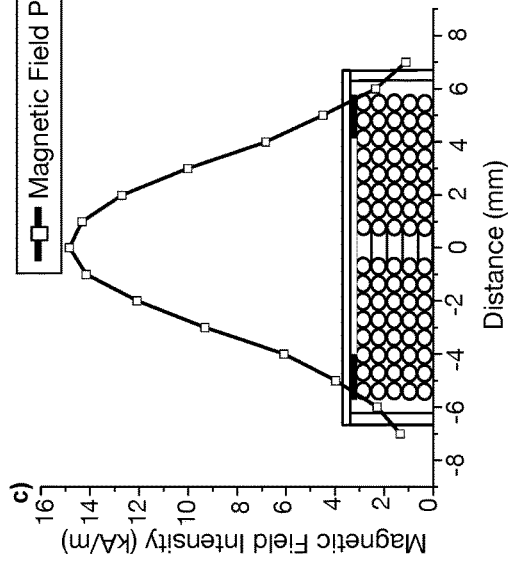

FIG. 5a illustrates the linearity of the magnetic field, at the central part of the surface of the polycarbonate sheet, as a function of the current through the coil. The current values shown were measured using a custom-made Rogowski coil current sensor. A maximum magnetic field of 15 kA/m was achieved with a 26.75 A current circulating through the coil. FIG. 5b, on the other hand, illustrates the exponential behavior that the magnetic field intensity possesses as a function of axial distance from the surface of the coil (squares). Since the magnetic field could not be measured on the coil surface, an exponential fit (triangles) was done and the unknown values were estimated. Since the polycarbonate sheet sealing the device had a thickness of 2.5 mm including the polycarbonate strips (delimited by the gray color) the magnetic field intensities at which the samples were exposed started at those distances. Therefore, the maximum magnetic field intensities at which samples were exposed ranged from 10-15 kA/m. Finally, FIG. 5c shows the radial magnetic field distribution at the surface of the polycarbonate sheet at the maximum current level. As can be appreciated, the plot from the laparoscopic instrument shows how quickly the magnetic field intensity decreases the farther an observer is from its center.

Induction Heating Experiments

To confirm the novel applicability of the instrument of the present invention, the heating performance of a metal sample was assessed. This initial test consisted in exposing a 12 mm stainless steel disk to the alternating magnetic field. Three thermocouples were attached to the disk (center, border, and the midpoint between these two) to record the temperature rise when exposed to a magnetic field. The disk was then placed at the center of the coil as close as possible to the polycarbonate surface and the temperature rise was measured in three different media including: air, water, and gelatin. The depth the magnetic field can reach is very important for medical applications, as the tissues of interest will have different thicknesses. Therefore, the disk was also subjected to the magnetic field at different axial distances.

FIGS. 6a-6c show the temperature rise of a 12 mm stainless steel disk (in different media) in presence of the magnetic field generated by the laparoscopic instrument 1 of the present invention. Specifically, FIG. 6a corresponds to the test where the disk was left in air medium and, as expected, the temperature rise was higher than for the gelatin and water media (FIGS. 6b and 6c, respectively). These curves represent the temperature rise of the disk at specified distances from the surface of the coil, millimeter by millimeter (0 to 5 mm). The longer the distance from coil to load, the lower the temperature rise that the disk presented, thus confirming that the magnetic field can still affect a metal piece at longer distances, though at a lower magnetic field intensity. The temperature of the coil (dashed line) was maintained at approximately 14° C. with cold water. However, it is important to note that the temperature of the coil could be maintained at about between 5° C.-20° C. depending on the heating application and the type of cooling agent used, wherein it should be noted that small deviations from these limits due to factors such as but not limited to tolerances of the equipments are also encompassed by said range.

A comparison of these temperature rates at a 1 mm distance from the coil, per media, is illustrated in FIG. 6d. Temperature rise was higher for air and lower for water. FIGS. 6e and 6f correspond to the tests where the disk was exposed to the maximum magnetic field that the device could generate (15 kA/m at 289 kHz) at 1 mm and 5 mm distance, respectively. Only air (squares) and water (circles) are compared here, since gelatin melts at temperatures above 40° C. This test confirms that the generated magnetic field could heat a stainless-steel disk by means of magnetic induction.

A second test was carried out involving the use of uncoated superparamagnetic iron oxide nanoparticles (SPIONs) synthesized by a modified, optimized co-precipitation method. The purpose of this test was to assess whether there would be a temperature rise in presence of a magnetic field intensity of 15 kA/m at 289 kHz. A volume of 200 µL of uncoated SPIONs was added in the 14 mm diameter cavity of a 50 mm imaging dish from MatTek Corporation®. The cavity had a depth of 2 mm. The same test was conducted with water to determine if there was heat being transferred from the coil to the water sample.

FIG. 6g illustrates the behavior of magnetic nanoparticles and water in the presence of a magnetic field intensity of 15 kA/m at 289 kHz. On this plot, it can be observed that magnetic nanoparticles were dissipating heat during the application of the external alternating magnetic field. A temperature rise from 15° C. to 41° C. (in 2 minutes) was observed, therefore, dissipating heat to the environment. However, the water sample (downward triangles) presented an insignificant temperature rise from 15° C. to 18° C. confirming that little to no heat was being transferred from the coil to the sample.

Discussion

Induction heating strongly depends on the uniformity and intensity of the magnetic field to which the sample is exposed. In that regard, results from the magnetic field profile for the instrument of the present invention were presented in FIGS. 5a-5c. Since a pancake coil configuration was used, the uniformity of the magnetic field is lost the farther the observer is from the center of the coil, in any direction, as illustrated in FIGS. 5b and 5c. However, for medical application such as laparoscopic procedures this type of coil is the most adequate. The field would be strong enough to actuate either on magnetic fluids or any other device requiring heating.

Induction heating experiments were conducted on a 12 mm stainless steel disk in different media and at different distances from the magnetic field generator, which are very important for biomedical experiments. The present invention confirms that the inventive instrument heats at short distances, by magnetic induction. This shows that the instrument of the present invention can be applied to surfaces, be it a biological tissue or a metal sample. Moreover, since the preferred embodiment is a laparoscopic instrument it has the advantage of treating deep-seated tumors or heating a metal piece within a patient's body. FIGS. 6a-6c show that the magnetic field generated can still affect loads at farther distances from the coil's surface, but lower magnetic fields will be applied. Accordingly, this limitation can be compensated by increasing the magnetic field intensity.

Uncoated SPIONs with a total particle concentration of 100 mg/mL were used to observe what temperatures could be achieved in the bulk solution when exposed to a 15 kA/m magnetic field intensity. Even though a stainless-steel disk could heat in presence of the magnetic field (FIGS. 6a-6g), results showed a different scenario for the nanoparticles since the nanoparticles present a smaller load to the induction heater than the disk. In experiments with the laparoscopic instrument of the present invention, uncoated SPION solutions (360 to 500 µL) having concentrations of 0.6, 1.2, 5.0, 7.5, and 10 mg/mL, did not exhibit a perceptible temperature rise in presence of magnetic fields ranging from 10 to 15 kA/m. However, a concentration of 100 mg/mL did exhibit an increase in temperature at these intensities, but barely at the 40° C. to 50° C. expectation. These lower than expected temperature rises were due to the small volume of nanoparticles used. Also, due to the geometry of the coil used and its magnetic field exponential behavior with increasing distance, it is impossible to expose the whole sample to the same magnetic field intensity. This is true if the cavity of the plate used is filled completely with nanoparticle solution as in our experiments. Lowering the volume can also lower the heat dissipated, as there would be less nanoparticles per volume. This issue can be solved by using a helical coil which is widely used for MFH experiments, as the magnetic field is uniform inside of the coil. However, it is important to note that such solution could not be used for laparoscopic surgical procedures, as the magnetic field is lost outside of the coil.

Figure 8:
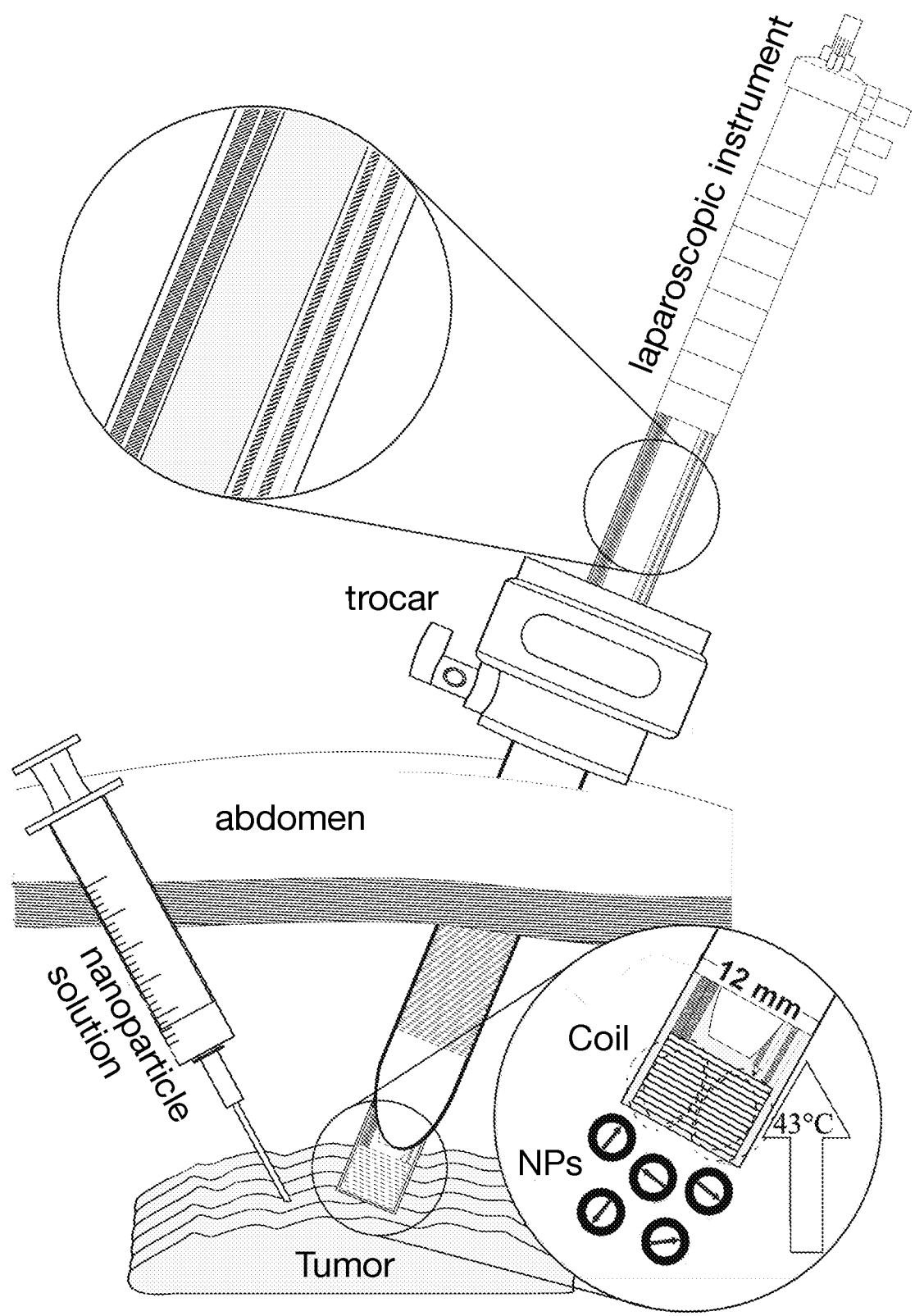
FIG. 8 illustrates the laparoscopic instrument used for a magnetic fluid hyperthermia procedure, according to the present invention.

According to a preferred embodiment of the invention, the laparoscopic instrument is used in a medical application such as laparoscopic procedures as illustrated in FIG. 8. In operation, once the laparoscopic instrument is setup and the peristaltic pump is turned on, water starts filling the interior of the instrument through, until it reaches the top, and exits. The laparoscopic instrument would be inserted through a trocar (like in laparoscopy) and would be directed to the tumor of interest. With the aid of magnetic nanoparticles and their heat dissipation mechanisms, the tumor temperature is increased until hyperthermic temperature is reached (~43° C.).

Because many varying and differing embodiments may be made within the scope of the inventive concept herein taught and because many modifications may be made in the embodiment herein detailed in accordance with the descriptive requirement of the law, it is to be understood that the details herein are to be interpreted as illustrative and not in a limiting sense. This specification and the accompanying drawings disclosed several preferred embodiments as examples of the invention. The invention is not intended to be limited to the embodiments illustrated. Numerous modifications, changes, variations, substitutions and equivalents will be apparent to those skilled in the art without departing from the spirit and scope of the present invention as described in the claims.

We claim:

1. A miniature inductive heating device comprising:
   an elongated body having a proximal end wall and a distal end wall opposite to said proximal end wall;

a multilayer pancake coil positioned inside the elongated body and in contact with said distal end wall;

a first thermal sensor positioned inside said multilayer pancake coil;

a second thermal sensor positioned inside said elongated body;

a cooling agent inlet port and a cooling agent outlet port positioned at the proximal end of said elongated body;

an electric wiring port positioned at the proximal end of said elongated body, wherein electrical cables from said first thermal sensor, said second thermal sensor and said multilayer pancake coil exit said elongated body through said electric wiring port;

a cooling agent contained inside said elongated body and being in contact with said multilayer pancake coil, wherein said cooling agent enters said elongated body through said cooling agent inlet port and exits said elongated body through said cooling agent outlet port.

2. The miniature inductive heating device of claim 1, wherein the cooling agent inlet port is positioned along a longitudinal axis of said elongated body.

3. The miniature inductive heating device of claim 1, wherein the cooling agent inlet port is positioned perpendicular to a longitudinal axis of said elongated body.

4. The miniature inductive heating device of claim 1, wherein the electric wiring port is positioned along a longitudinal axis of said elongated body.

5. The miniature inductive heating device of claim 1, wherein the electric wiring port is positioned perpendicular to a longitudinal axis of said elongated body.

6. The miniature inductive heating device of claim 1, wherein the cooling agent outlet port is positioned perpendicular to a longitudinal axis of said elongated body.

7. The miniature inductive heating device of claim 1, wherein said elongated body is made of a polymeric material.

8. The miniature inductive heating device of claim 1, wherein said distal end wall is made of a polymeric material.

9. The miniature inductive heating device of claim 1, wherein said first and second thermal sensors are thermistors.

10. The miniature inductive heating device of claim 1, wherein the multilayer pancake coil generates a magnetic field intensity of up to 30 kA/m at a frequency of 100-500 kHz.

11. The miniature inductive heating device of claim 1, wherein said multilayer pancake coil has an outer diameter of about 8-11 mm.

12. The miniature inductive heating device of claim 1, wherein the temperature of said multilayer pancake coil is maintained at about 5° C.-20° C.

13. The miniature inductive heating device of claim 1, wherein said cooling agent inlet port is connected to a cooling agent pump and said cooling agent outlet port is connected to a cooling agent reservoir.

14. The miniature inductive heating device of claim 1, wherein said cooling agent is water.

15. The miniature inductive heating device of claim 1, wherein said cooling agent is maintained a temperature between about −15° C.-20° C.

16. The miniature inductive heating device of claim 1, wherein said cooling agent inlet port further comprises a cooling agent tube positioned inside said elongated body so that an output of said cooling agent tube is in close proximity to said multilayer pancake coil.

17. The miniature inductive heating device of claim 16, wherein the second thermal sensor is positioned at the output of said cooling agent tube.

18. The miniature inductive heating device of claim 1, wherein the electrical cables from said multilayer pancake coil are connected to an impedance matching circuit and the electrical cables from said first and second thermal sensors are connected to a data acquisition system.

19. The miniature inductive heating device of claim 18, further comprising a signal waveform generator device providing a signal to said impedance matching circuit.

20. The miniature inductive heating device of claim 18, further comprising a processing unit receiving from said data acquisition system temperature data associated to temperature measurements of said first and second thermal sensors and further controlling at least one of: the flow rate of said cooling agent, the temperature of said cooling agent and the power provided to said multilayer pancake coil.

* * * * *